United States Patent
Wang et al.

(10) Patent No.: US 11,100,639 B2
(45) Date of Patent: Aug. 24, 2021

(54) METHOD FOR SKIN EXAMINATION BASED ON RBX COLOR-SPACE TRANSFORMATION

(71) Applicant: H-SKIN AESTHETICS CO., LTD., Kaohsiung (TW)

(72) Inventors: Chih-Yu Wang, Kaohsiung (TW);
Po-Han Huang, Kaohsiung (TW);
Shu-Chen Chang, Kaohsiung (TW);
Chia-Chen Lu, Kaohsiung (TW);
Wen-Chien Tsai, Kaohsiung (TW);
Yun-Hsuan Ou Yang, Kaohsiung (TW)

(73) Assignee: H-SKIN AESTHETICS CO., LTD., Kaohsiung (TW)

( * ) Notice: Subject to any disclaimer, the term of this patent is extended or adjusted under 35 U.S.C. 154(b) by 140 days.

(21) Appl. No.: 16/709,358

(22) Filed: Dec. 10, 2019

(65) Prior Publication Data

US 2020/0184642 A1 Jun. 11, 2020

Related U.S. Application Data

(60) Provisional application No. 62/777,772, filed on Dec. 11, 2018.

(51) Int. Cl.
| | | |
|---|---|---|
| *G06T 7/00* | (2017.01) | |
| *G06T 7/136* | (2017.01) | |
| *G06T 7/90* | (2017.01) | |
| *A61B 5/00* | (2006.01) | |

(52) U.S. Cl.
CPC ............ *G06T 7/0012* (2013.01); *A61B 5/445* (2013.01); *G06T 7/136* (2017.01); *G06T 7/90* (2017.01); *G06T 2207/10024* (2013.01); *G06T 2207/20021* (2013.01); *G06T 2207/30088* (2013.01)

(58) Field of Classification Search
CPC ......... G06T 7/0012; G06T 7/136; G06T 7/90; G06T 2207/20021; G06T 2207/30088; G06T 2207/10024; G06T 2200/24; G06T 7/0016; A61B 5/445; A61B 5/4848; A61B 5/0075; A61B 5/0077; A61B 5/1032
See application file for complete search history.

(56) References Cited

U.S. PATENT DOCUMENTS 6,081,612 A * 6/2000 Gutkowicz-Krusin ...................... A61B 5/0071
382/128
7,233,693 B2 * 6/2007 Momma .............. A61B 5/0064
382/162

(Continued)

OTHER PUBLICATIONS

RBX® Technology Overview. Published 2007 Ramazan Demirli, Ph.D.; Paul Otto, Ph.D.; Ravi Viswanathan, M.S.; Sachin Patwardhan, Ph.D.; Jim Larkey, M.B.A. (Year: 2007).*

(Continued)

*Primary Examiner* — Vu Le
*Assistant Examiner* — Winta Gebreslassie
(74) *Attorney, Agent, or Firm* — WPAT, PC

(57) ABSTRACT

The present invention discloses a method for detecting skin conditions, and the method includes the steps of: capturing a skin image from a suspected subject; decomposing the skin image into an RBX image through RBX color-space transformation; and determining skin condition of the subject according to a parameter of a color model of the RBX image.

6 Claims, 13 Drawing Sheets

(56) References Cited

U.S. PATENT DOCUMENTS

| | | | | |
|---|---|---|---|---|
| 8,498,460 | B2* | 7/2013 | Patwardhan | A61B 5/0077 |
| | | | | 382/128 |
| 10,368,795 | B2* | 8/2019 | Patwardhan | A61B 5/0077 |
| 10,702,160 | B2* | 7/2020 | Patwardhan | G06K 9/00 |
| 2011/0206254 | A1* | 8/2011 | Patwardhan | A61B 5/0077 |
| | | | | 382/128 |
| 2019/0133513 | A1* | 5/2019 | Patwardhan | A61B 5/0077 |
| 2019/0298252 | A1* | 10/2019 | Patwardhan | A61B 5/0082 |
| 2020/0380674 | A1* | 12/2020 | Ding | G06T 7/0012 |

OTHER PUBLICATIONS

Search & Discovery Research At ISU & EDA, vol. 29, pp. 44-49 (2016).

* cited by examiner

METHOD FOR SKIN EXAMINATION BASED ON RBX COLOR-SPACE TRANSFORMATION

CROSS REFERENCE

This non-provisional application claims benefit of American Provisional Application No. 62/777,772, filed on Dec. 11, 2018, the contents thereof are incorporated by reference herein.

FIELD OF THE INVENTION

The present invention is related to a method for skin examination, and more particularly to a method for skin examination based on RBX color-space transformation.

BACKGROUND OF THE INVENTION

RBX color-space transformation is developed by Canfield Imaging Systems. As shown in FIG. 1, a color image is represented in terms of color signatures Red denoting hemoglobin components and Brown denoting melanin components. As shown in FIG. 2, a color image is decomposed into a Red component image showing hemoglobin distribution and a Brown component image showing melanin distribution. Additionally, hemoglobin is distributed in the dermis layer of skin, and melanin is distributed between the dermis layer and the epidermis layer of skin. Polarized light is preferably adopted for taking the images because the cross-polarized image can eliminate the specular reflection of the skin, present the color below the stratum corneum, and display the texture of the skin more clearly. (FIG. 3).

SEARCH & DISCOVERY RESEARCH AT ISU & EDH, vol. 29, pages 44-49, 2016 discloses while the average blue color intensity in the Red component image obtained through RBX color-space transformation is lower, the corresponding subject's rosacea severity is higher; otherwise the opposite is true. This result can facilitate doctors to determine the severity of rosacea.

Accordingly, there is need for people skilled in this art to increase the clinical applicability of RBX color-space transformation.

SUMMARY OF THE INVENTION

A first embodiment of the present invention provides a method for detecting skin condition, and the method includes the steps of: capturing a skin image from a suspected subject; decomposing the skin image into an RBX image through RBX color-space transformation; and determining skin condition of the subject according to a parameter of a color model of the RBX image.

Preferably, the captured skin image is a color image.

Preferably, the color model is RGB, HSL, HSV (or named as HSB), CMYK, or LAB.

Preferably, the skin condition is degree of skin redness, skin whitening degree, or skin fleck degree.

Preferably, the skin redness is related to a skin disease with vascular involvement including inflammatory dermatoses or a skin disease with vascular dilation but no inflammation, and each skin disease is rosacea, psoriasis, atopic dermatitis, facial eczema, sensitive skin of face, seborrheic dermatitis, dermatophytosis, pityriasis versicolor, hemangioma, aging skin with vessel dilation, skin cancer, acne, seborrheic keratosis, or telangiectasia.

Preferably, the skin image decomposing and the skin condition determining are individually performed in a human machine interface device.

Preferably, the skin image capturing is performed in a human machine interface device.

Preferably, the human machine interface device is a desktop computer, a notebook computer, a tablet, a mobile phone, or a personal digital assistant (PDA).

A second embodiment of the present invention provides a method for detecting skin condition, and the method includes the steps of: capturing a skin image from a suspected subject; decomposing the skin image into a Red component image through RBX color-space transformation; calculating an average red intensity value and an average green intensity value from the Red component image; subtracting the average red intensity value from the average green intensity value to obtain an R-G value; and comparing the R-G value of the suspected subject with another R-G value of a reference subject, wherein while the R-G value of the suspected subject is greater than that of the reference subject, skin condition of the suspected subject is poorer than that of the reference subject; while the R-G value of the suspected subject is smaller than that of the reference subject, skin condition of the suspected subject is better than that of the reference subject.

Preferably, the captured skin image is a color image.

Preferably, the skin condition is degree of skin redness, skin whitening degree, or skin fleck degree.

Preferably, the skin redness is related to a skin disease with vascular involvement including inflammatory dermatoses or a skin disease with vascular dilation but no inflammation, and each skin disease is rosacea, psoriasis, atopic dermatitis, facial eczema, sensitive skin of face, seborrheic dermatitis, dermatophytosis, pityriasis versicolor, hemangioma, aging skin with vessel dilation, skin cancer, acne, seborrheic keratosis, or telangiectasia.

Preferably, the skin image decomposing, the average intensity value calculating, the R-G value obtaining, and the R-G value comparing are individually performed in a human machine interface device.

Preferably, the skin image capturing is performed in a human machine interface device.

Preferably, the human machine interface device is a desktop computer, a notebook computer, a tablet, a mobile phone, or a personal digital assistant.

A third embodiment of the present invention provides a method for detecting skin condition, and the method includes the steps of: capturing a skin image from a suspected subject; decomposing the skin image into a Red component image through RBX color-space transformation; calculating an average red intensity value and an average green intensity value from the Red component image; subtracting the average red intensity value from the average green intensity value to obtain an R-G value; and comparing the currently-obtained R-G value with another previously-obtained R-G value of the same subject, wherein while the currently-obtained R-G value is greater than the previously-obtained one, the suspected subject shows poor tendency for skin condition; while the currently-obtained R-G value is smaller than the previously-obtained one, the suspected subject shows good tendency for skin condition.

Preferably, the captured skin image is a color image.

Preferably, the skin condition is degree of skin redness, skin whitening degree, or skin fleck degree.

Preferably, the skin redness is related to a skin disease with vascular involvement including inflammatory dermatoses or a skin disease with vascular dilation but no inflammation, and each skin disease is rosacea, psoriasis, atopic dermatitis, facial eczema, sensitive skin of face, seborrheic dermatitis, dermatophytosis, pityriasis versicolor, hemangioma, aging skin with vessel dilation, skin cancer, acne, seborrheic keratosis, or telangiectasia.

Preferably, the currently-obtained R-G value is an R-G value obtained following treatment, and the previously-obtained one is an R-G value obtained prior to treatment.

Preferably, the skin image decomposing, the average intensity value calculating, the R-G value obtaining, and the R-G value comparing are individually performed in a human machine interface device.

Preferably, the skin image capturing is performed in a human machine interface device.

Preferably, the human machine interface device is a desktop computer, a notebook computer, a tablet, a mobile phone, or a personal digital assistant.

A fourth embodiment of the present invention provides a method for diagnosing rosacea, and the method includes the steps of: capturing a skin image from a suspected subject; decomposing the skin image into a Red component image through RBX color-space transformation; calculating an average red intensity value and an average green intensity value from the Red component image; and subtracting the average red intensity value from the average green intensity value to obtain an R-G value, wherein while the R-G value is of less than 72 (<72), the subject is not suffered from rosacea; while the R-G value is of more than and equal to 72 and of less than 82 (>72 and <82), the subject is suffered from mild rosacea; while the R-G value is of more than and equal to 82 and of less than 92 (>82 and <92), the subject is suffered from moderate rosacea; while the R-G value is of more than and equal to 92 (>92), the subject is suffered from severe rosacea.

Preferably, the captured skin image is a color image.

Preferably, the skin image decomposing, the average intensity value calculating, and the R-G value obtaining are individually performed in a human machine interface device.

Preferably, the skin image capturing is performed in a human machine interface device.

Preferably, the human machine interface device is a desktop computer, a notebook computer, a tablet, a mobile phone, or a personal digital assistant.

A fifth embodiment of the present invention provides a method for estimating skin therapy effect, and the method includes the steps of: decomposing a skin image obtained prior to skin therapy and another skin image obtained following skin therapy through RBX color-space transformation respectively into a Brown component image prior to skin therapy and another Brown component image following skin therapy; performing gray processing on the Brown component image prior to skin therapy and the Brown component image following skin therapy respectively to generate a grayscale image prior to skin therapy and another grayscale image following skin therapy; transforming the grayscale image prior to skin therapy and the grayscale image following skin therapy respectively into an intensity spectrum prior to skin therapy and another intensity spectrum following skin therapy; partitioning each intensity spectrum into a first block and a second block according to an intensity values, wherein the intensity value corresponding to the first block is greater than that corresponding to the second block; calculating an area of the first block in the intensity spectrum prior to skin therapy, an area of the second block in the intensity spectrum prior to skin therapy, an area of the first block in the intensity spectrum following skin therapy, and an area of the second block in the intensity spectrum following skin therapy; and dividing the area of the first block in the intensity spectrum prior to skin therapy by an area of total blocks in the intensity spectrum prior to skin therapy to generate a Pre-H ratio value, dividing the area of the second block in the intensity spectrum prior to skin therapy by the area of total blocks in the intensity spectrum prior to skin therapy to generate a Pre-L ratio value, dividing the area of the first block in the intensity spectrum following skin therapy by an area of total blocks in the intensity spectrum following skin therapy to generate a Post-H value, and dividing the area of the second block in the intensity spectrum following skin therapy by the area of total blocks in the intensity spectrum following skin therapy to generate a Post-L value, wherein while the Post-H value is greater than the Pre-H value and the Post-L value is less than the Pre-L value, it indicates that the skin therapy is effective.

Preferably, the captured skin image is a color image.

Preferably, the skin therapy is provided for improving degree of skin redness, enhancing skin whitening degree, or lowering skin fleck degree.

Preferably, the skin redness is related to a skin disease with vascular involvement including inflammatory dermatoses and a skin disease with vascular dilation but no inflammation, and each skin disease is rosacea, psoriasis, atopic dermatitis, facial eczema, sensitive skin of face, seborrheic dermatitis, dermatophytosis, pityriasis versicolor, hemangioma, aging skin with vessel dilation, skin cancer, acne, seborrheic keratosis, or telangiectasia.

Preferably, the skin fleck is nevus of Ota, melasma, or pigmented aging spots, including solar lentigines.

Preferably, the skin therapy is 755 nm picosecond toning laser therapy, 1064 nm picosecond toning laser therapy, or 755 nm picosecond spot laser therapy.

Preferably, any one of the foregoing steps is performed in a human machine interface device.

Preferably, the human machine interface device is a desktop computer, a notebook computer, a tablet, a mobile phone, or a personal digital assistant.

DETAILED DESCRIPTION OF THE INVENTION

The detailed description and preferred embodiments of the invention will be set forth in the following content, and provided for people skilled in the art to understand the characteristics of the invention.

Example 1

Dr. Po-Han Huang provided polarized skin pictures and non-polarized skin pictures obtained from 26 individuals. According to these non-polarized pictures, all individuals were classified into four groups: the normal group (n=2), the mild rosacea group (n=6), the moderate rosacea group (n=13), and the severe rosacea group (n=5).

Figure 1:
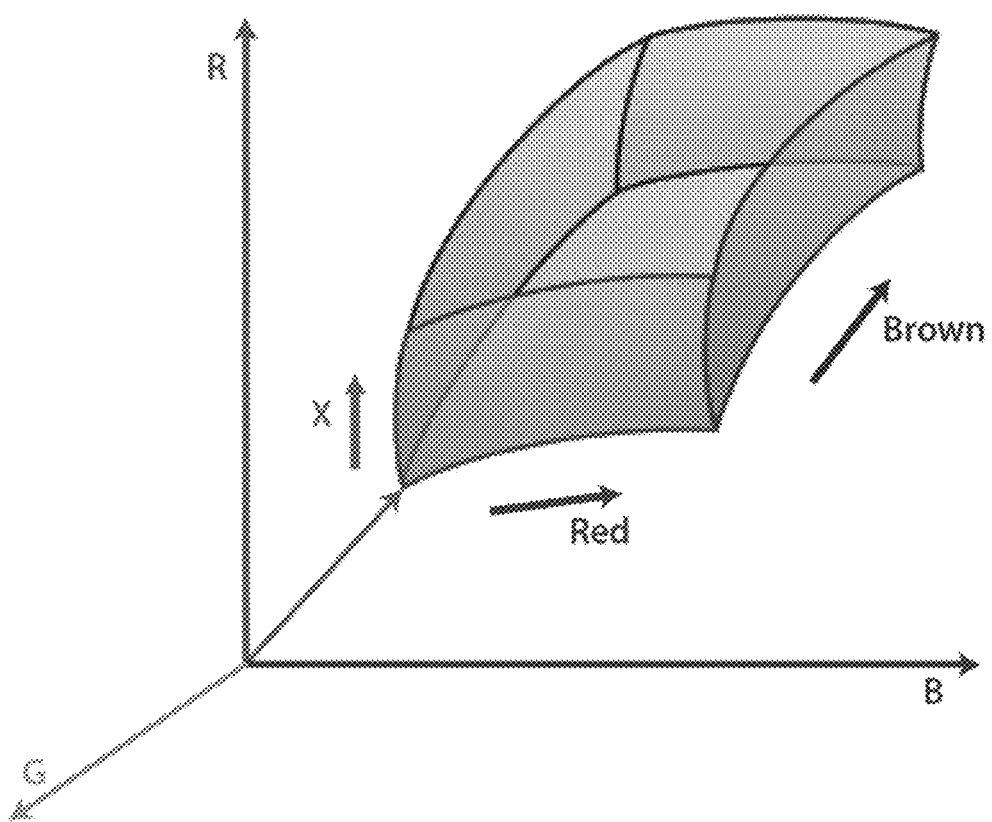
FIG. 1 is a schematic drawing showing the RBX color-space.
Figure 2:
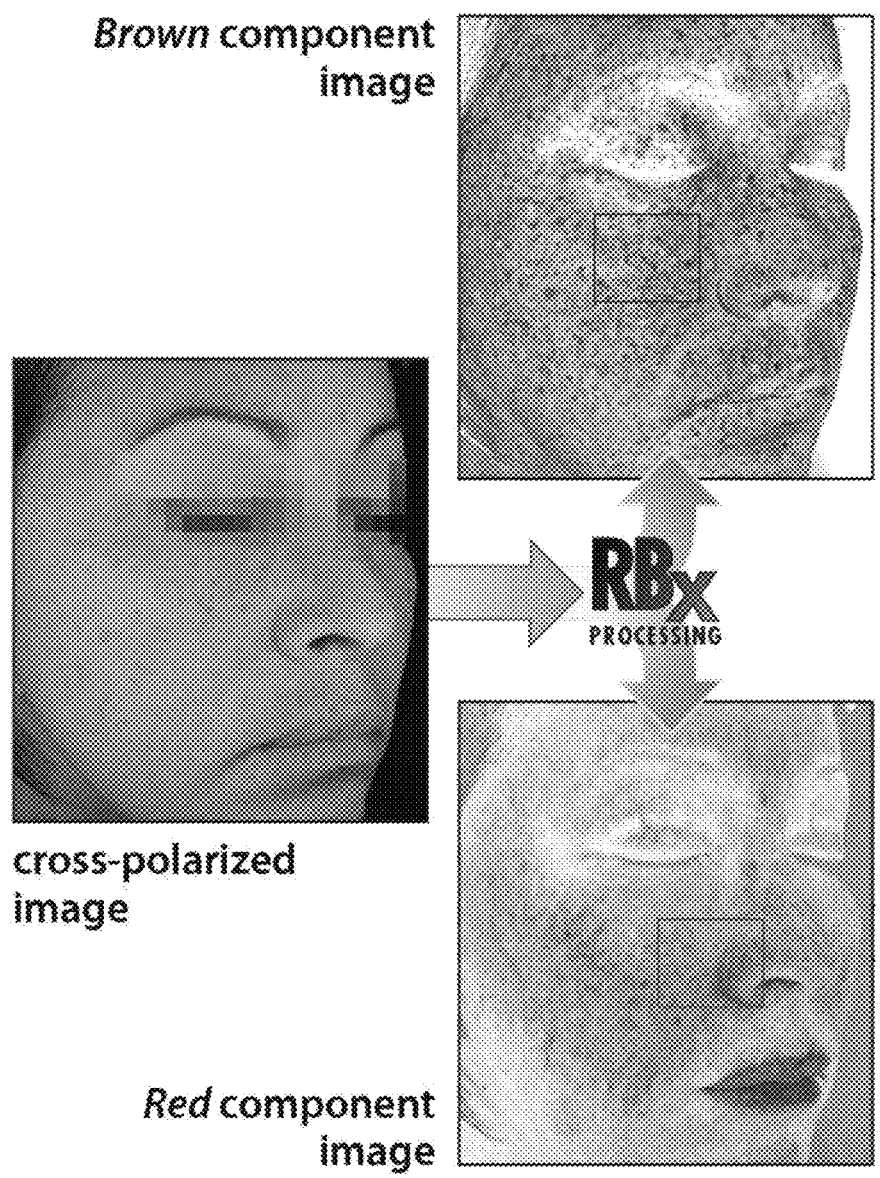
FIG. 2 is a schematic drawing showing a Red component image and a Brown component image obtained through RBX color-space transformation.
Figure 3:
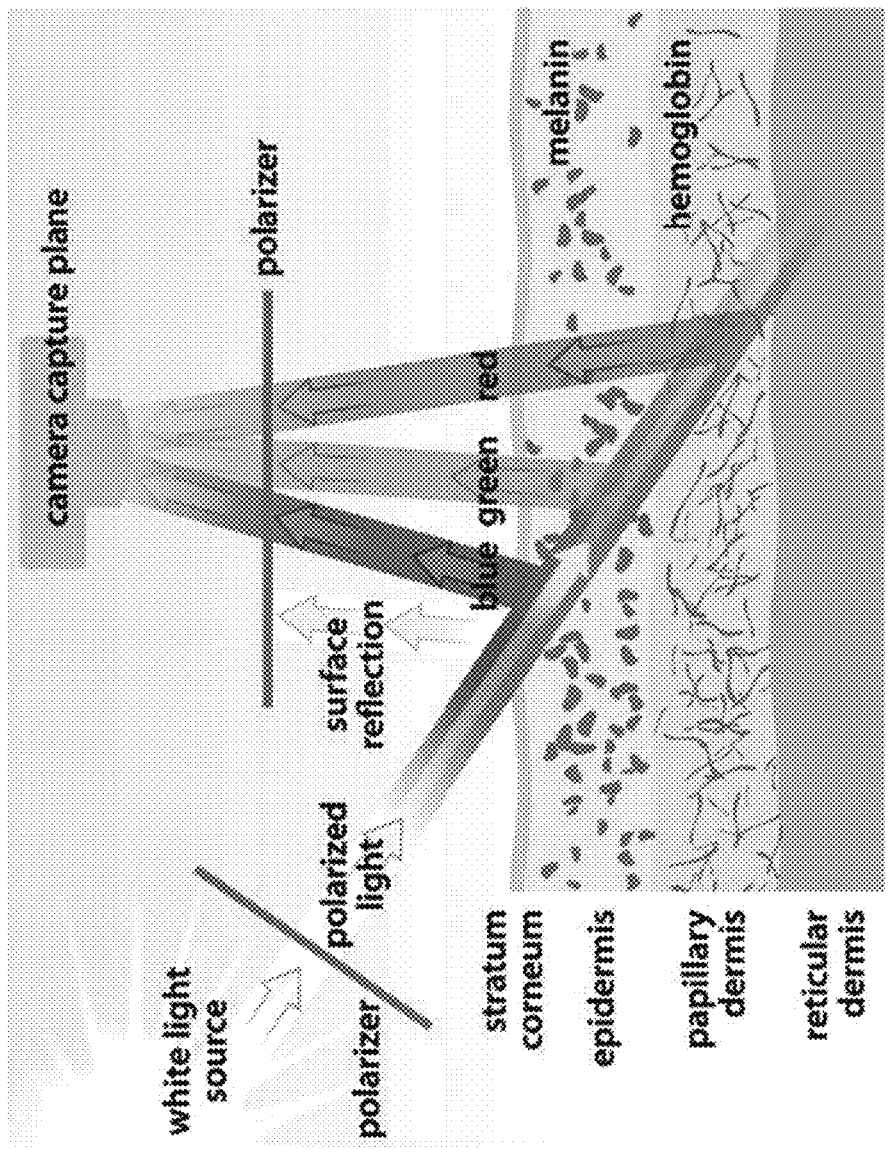
FIG. 3 is a schematic drawing illustrating that polarized light is used to capture a skin image.
Figure 4:
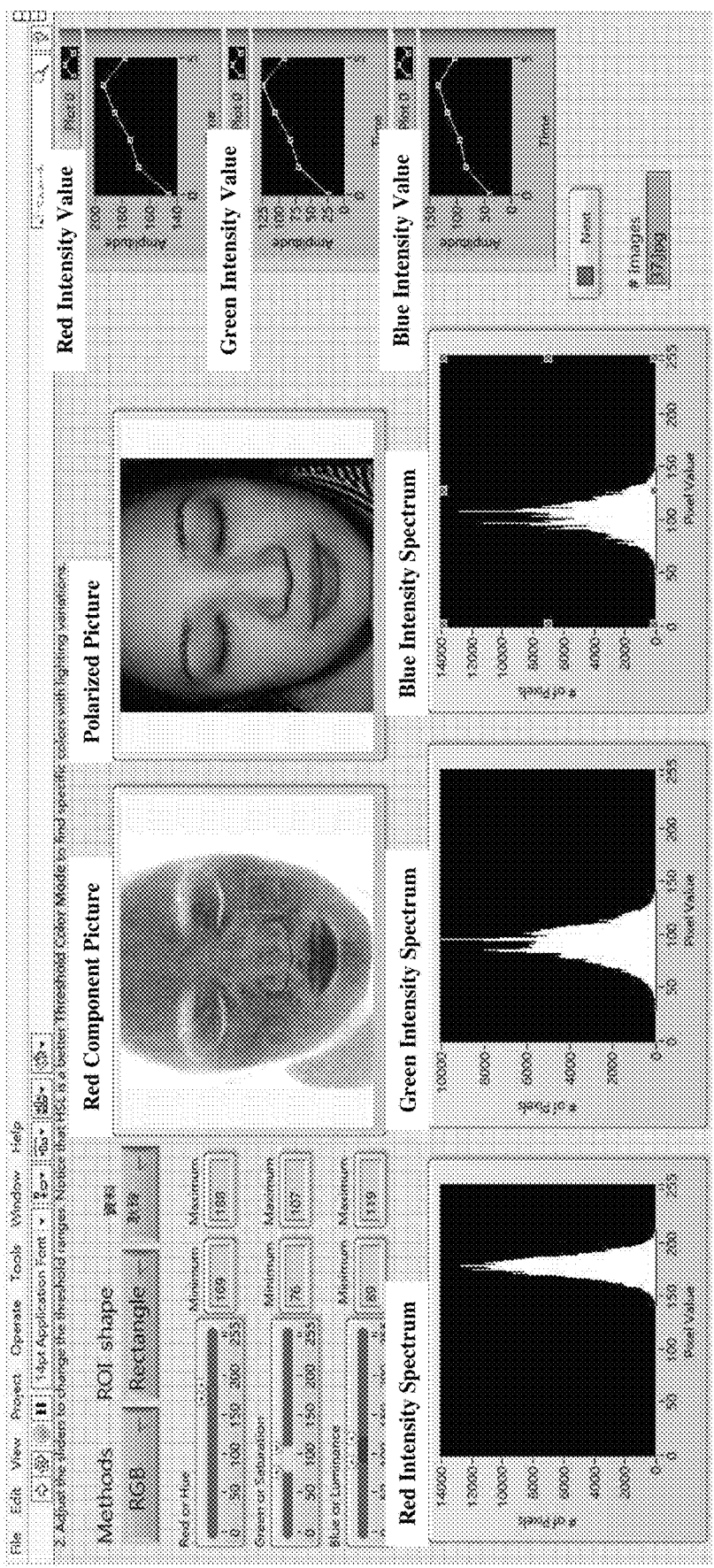
FIG. 4 is a drawing of an application page illustrating the operation for program written in accordance with Laboratory Virtual Instrumentation Engineering Workbench (LabVIEW)

All polarized pictures were converted into Red component pictures with RBX color-space transformation. These Red component pictures were then converted into red intensity spectra, green intensity spectra, and blue intensity spectra with the program written in accordance with LabVIEW shown in FIG. 4. Finally, average red intensity values, average green intensity values, and average blue intensity values were calculated from all intensity spectra.

Figure 5:
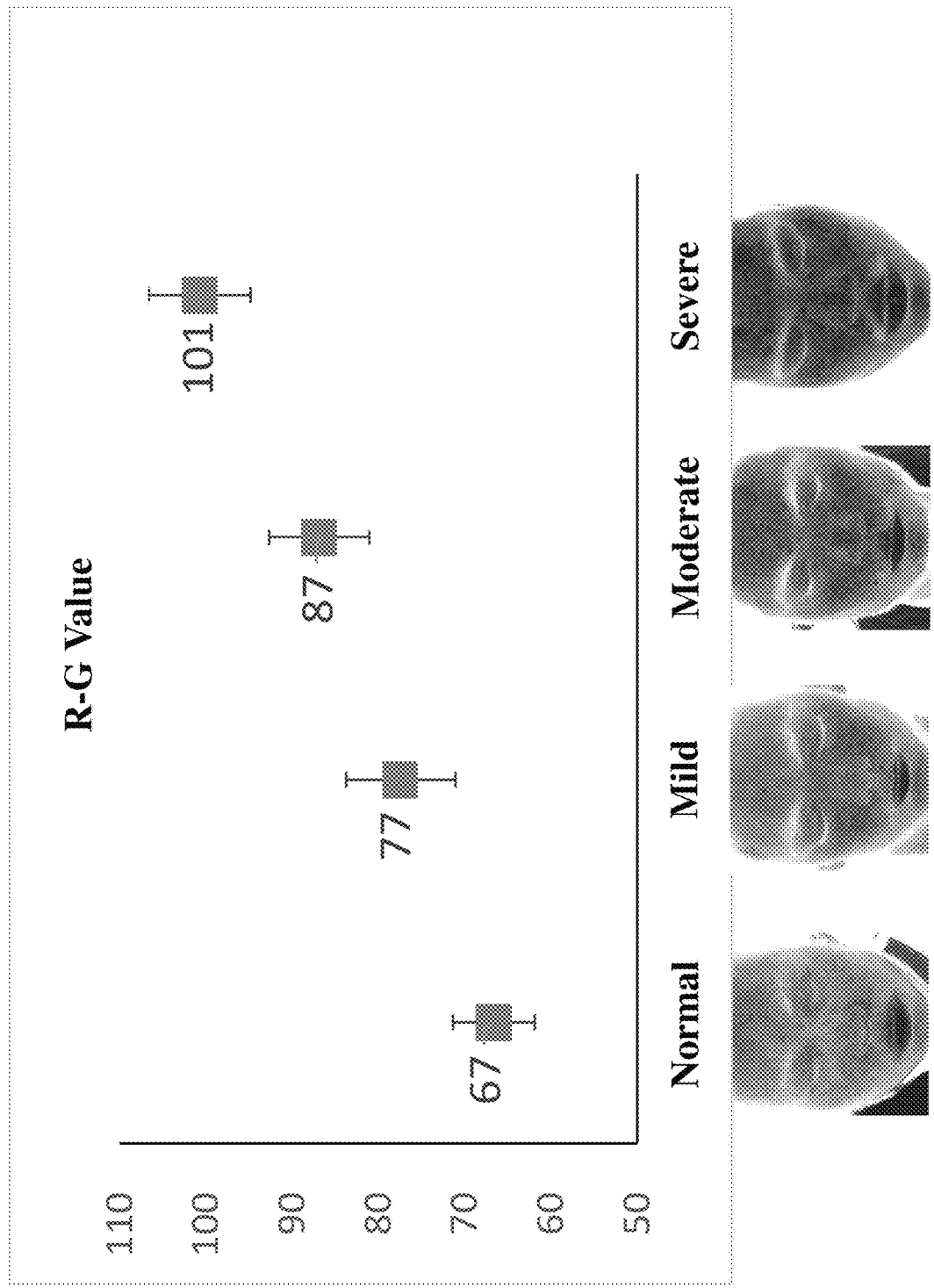
FIG. 5 is a statistical chart illustrating the R-G values of individuals of different types.

All individuals did not differ with respect to the average red intensity values. However, as shown in FIG. 5, according the difference of the average red intensity value minus the average green intensity value, namely the R-G value, the severe rosacea group, the moderate rosacea group, the mild rosacea group, the normal group are ranked from high to low. Specifically, the individuals of the normal group had a R-G value approximately of 67 (approximately in the range of 60-72); the individuals of the mild rosacea group had a R-G value approximately of 77 (approximately in the range of 72-82); the individuals of the moderate rosacea group had a R-G value approximately of 87 (approximately in the range of 82-92); the individuals of the severe rosacea group had a R-G value approximately of 101 (approximately in the range of 92-110).

As above, the bracket of the R-G value accords with the diagnosis result made with physicians' expertise, and therefore can be used as a reference for determining the disease severity.

Example 2

Dr. Po-Han Huang provided polarized skin pictures and non-polarized skin pictures from 4 individuals, and then numbered them as Nos. 1-4 respectively. All individuals were diagnosed according these non-polarized pictures, wherein individual No. 1 was suffered from severe rosacea, individual No. 2 was suffered from moderate rosacea, individual No. 3 was suffered from moderate rosacea, and individual No. 4 was suffered from mild rosacea. Afterwards, all individuals received treatment, and their polarized skin pictures and non-polarized skin pictures were captured on the specific day following treatment. All individuals' treatment condition was diagnosed according these non-polarized skin pictures, and according to the operation described in EXAMPLE 1, the R-G value prior to treatment and that following treatment of each individual were obtained.

Figure 6:
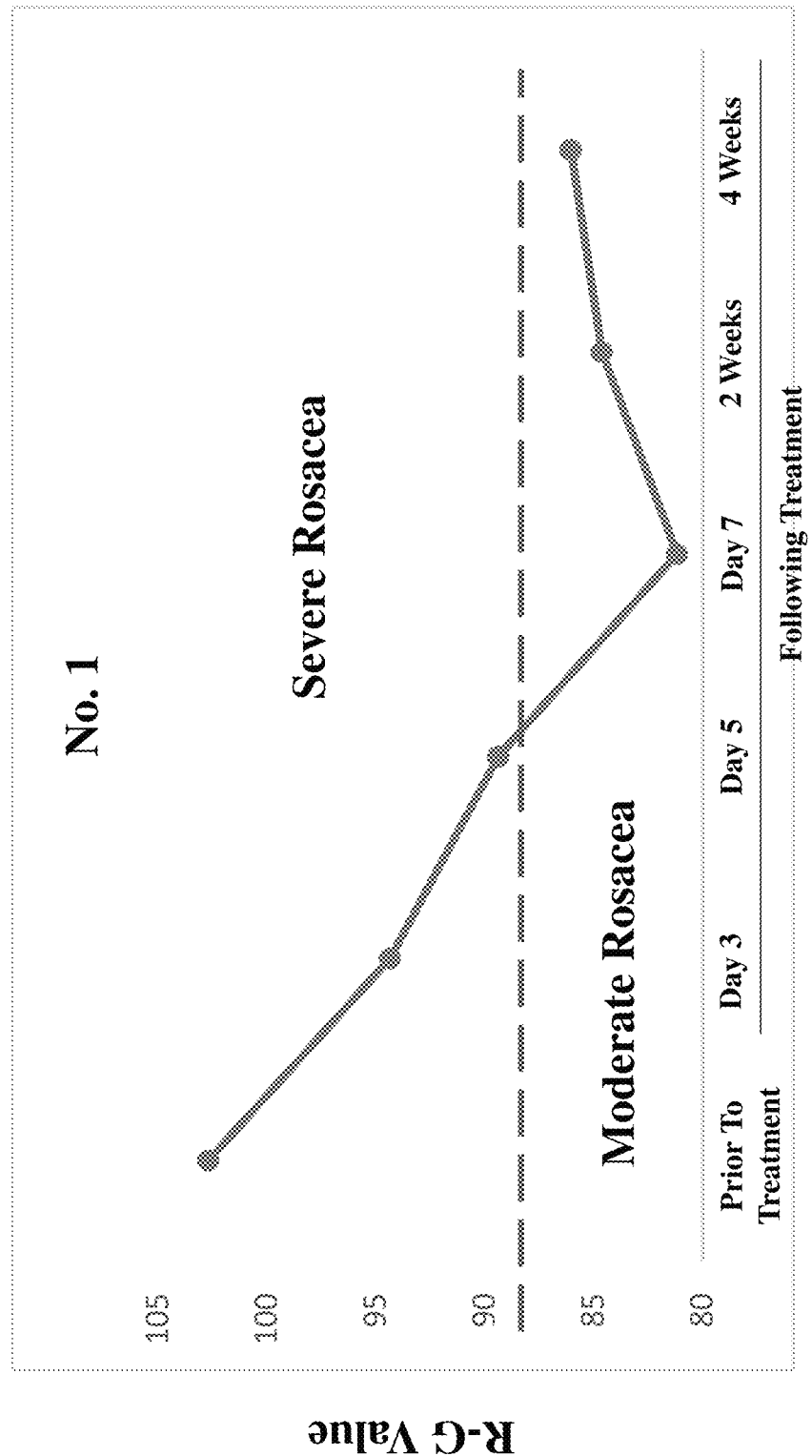
FIG. 6 is a statistical chart illustrating the R-G values of individual No. 1 prior to treatment and following treatment.

As shown in the non-polarized skin pictures, the disease condition of individual No. 1 became moderate on day 7 following treatment. As further shown in FIG. 6, the R-G value fell below a threshold of 87 on day 7 following treatment. The result indicates the R-G threshold of 87 can be used as a reference for physicians to evaluate disease severity after treatment.

Figure 7:
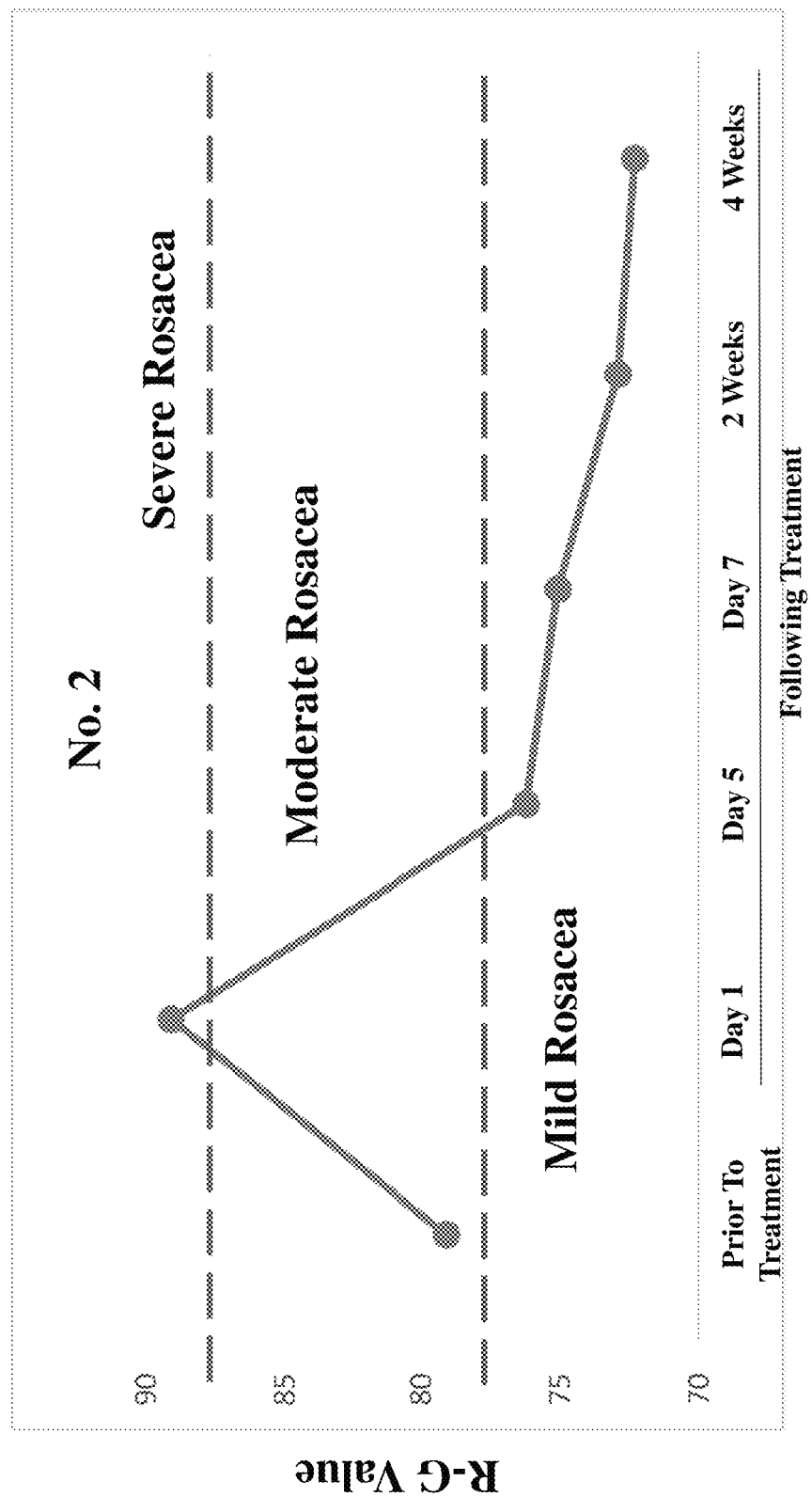
FIG. 7 is a statistical chart illustrating the R-G values of individual No. 2 prior to treatment and following treatment.

As shown in the non-polarized skin pictures, the disease condition of individual No. 2 became severe on day 1 following treatment and then became mild on day 6 following treatment. As further shown in FIG. 7, the R-G value exceeded a threshold of 87 on day 1 following treatment and the R-G value fell below a threshold of 77 on day 5 following treatment. The result indicates the R-G threshold of 87 and the R-G threshold of 77 can be used as a reference for physicians to evaluate disease severity after treatment.

Figure 8:
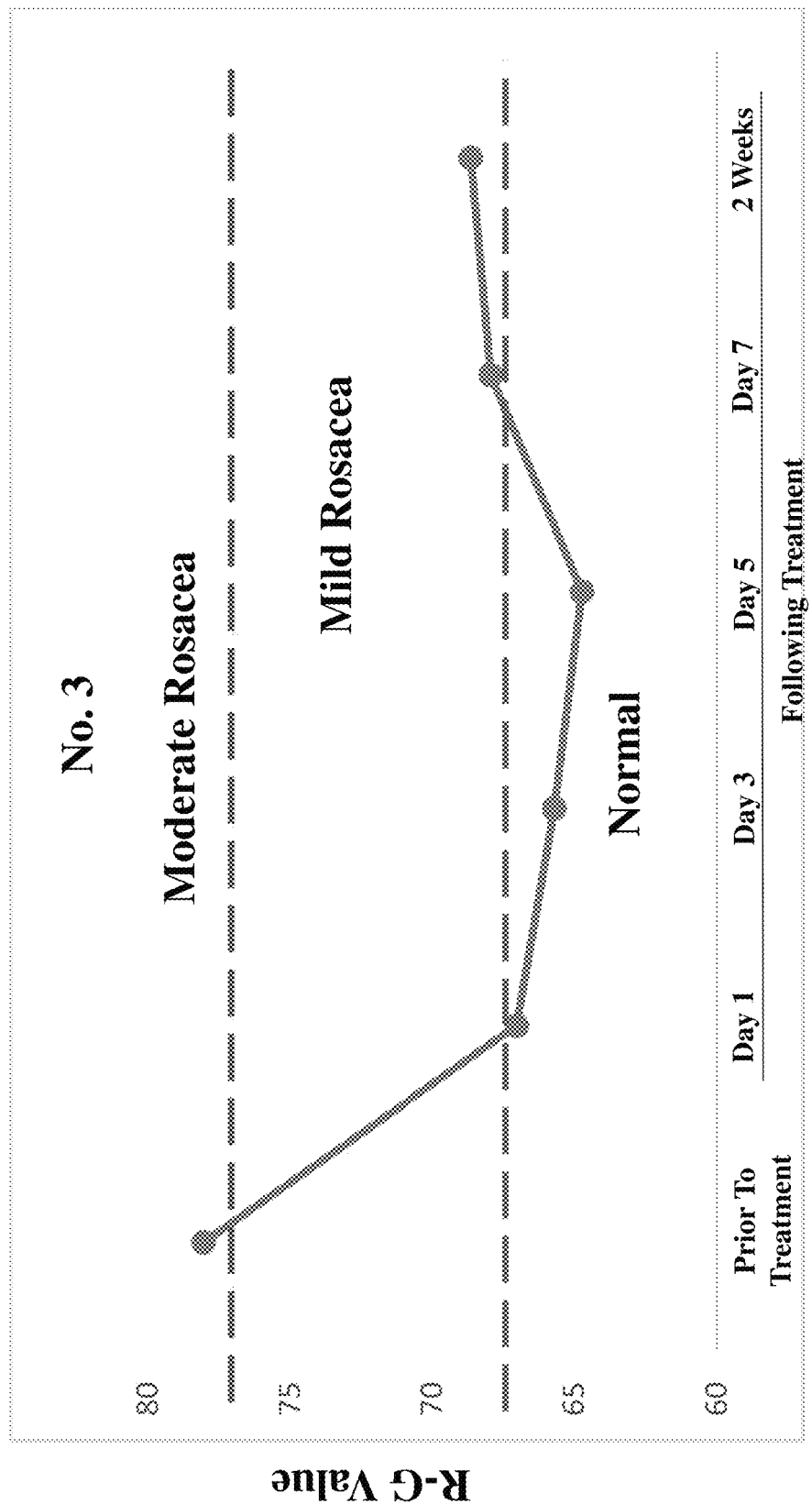
FIG. 8 is a statistical chart illustrating the R-G values of individual No. 3 prior to treatment and following treatment.

As shown in the non-polarized skin pictures, the disease condition of individual No. 3 became normal before day 7 following treatment and then became worse after day 7 following treatment. As further shown in FIG. 8, the R-G value fell below a threshold of 67 from day 1 to day 6 following treatment and the R-G value exceeded a threshold of 67 after day 7 following treatment. The result indicates the R-G threshold of 67 can be used as a reference for the physicians to evaluate disease severity after treatment.

Figure 9:
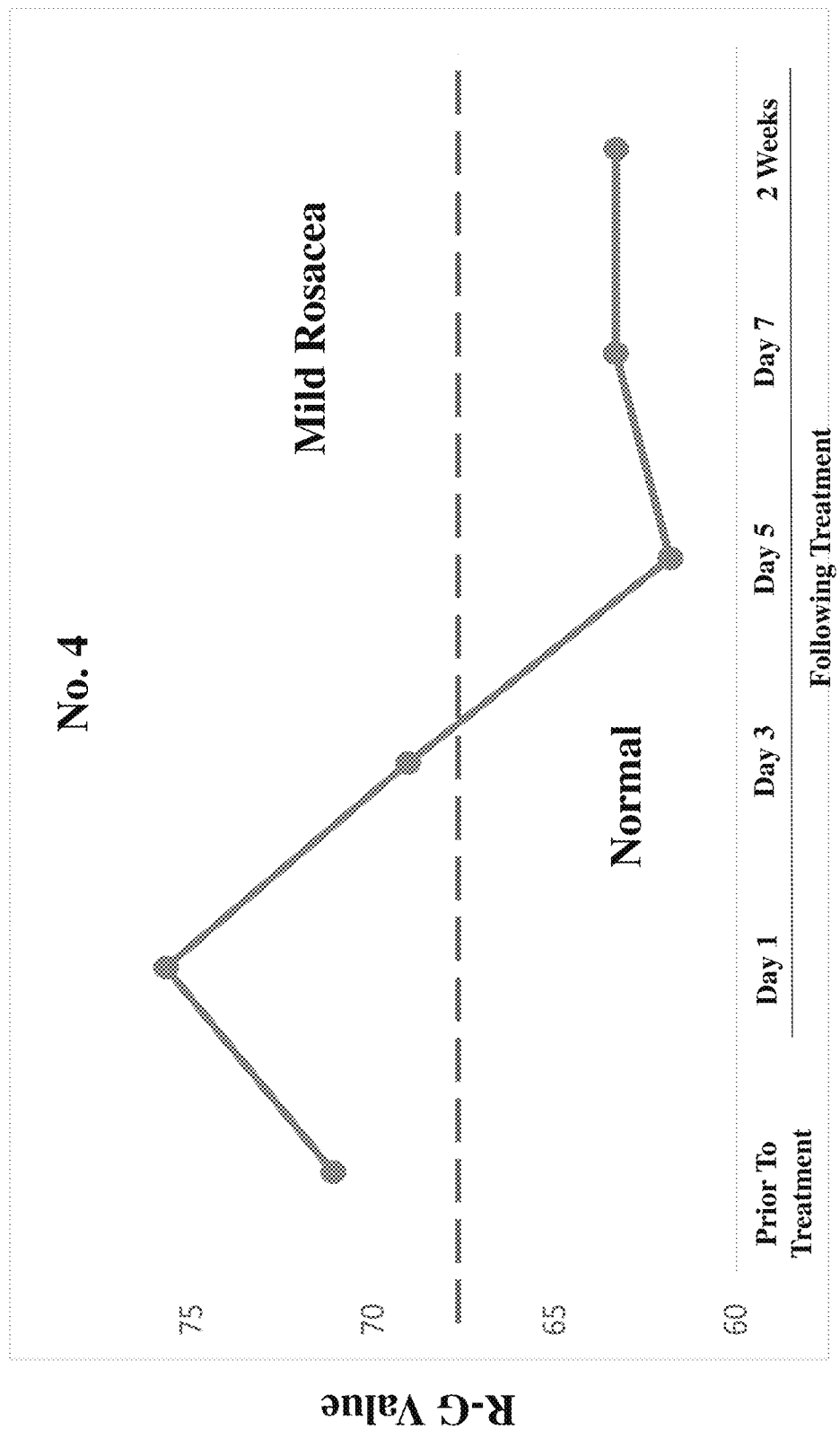
FIG. 9 is a statistical chart illustrating the R-G values of individual No. 4 prior to treatment and following treatment.

As shown in the non-polarized skin pictures, the disease condition of individual No. 4 became normal on day 5 following treatment. As further shown in FIG. 9, the R-G value fell below a threshold of 67 on day 5 following treatment. The result indicates the R-G threshold of 67 can be used as a reference for physicians to evaluate disease severity after treatment.

As above, the bracket of the R-G value accords with the diagnosis result made with the physicians' expertise, and therefore can be used as a reference for determining the disease severity based on intensity of redness of the skin degree.

Example 3

Figure 10:
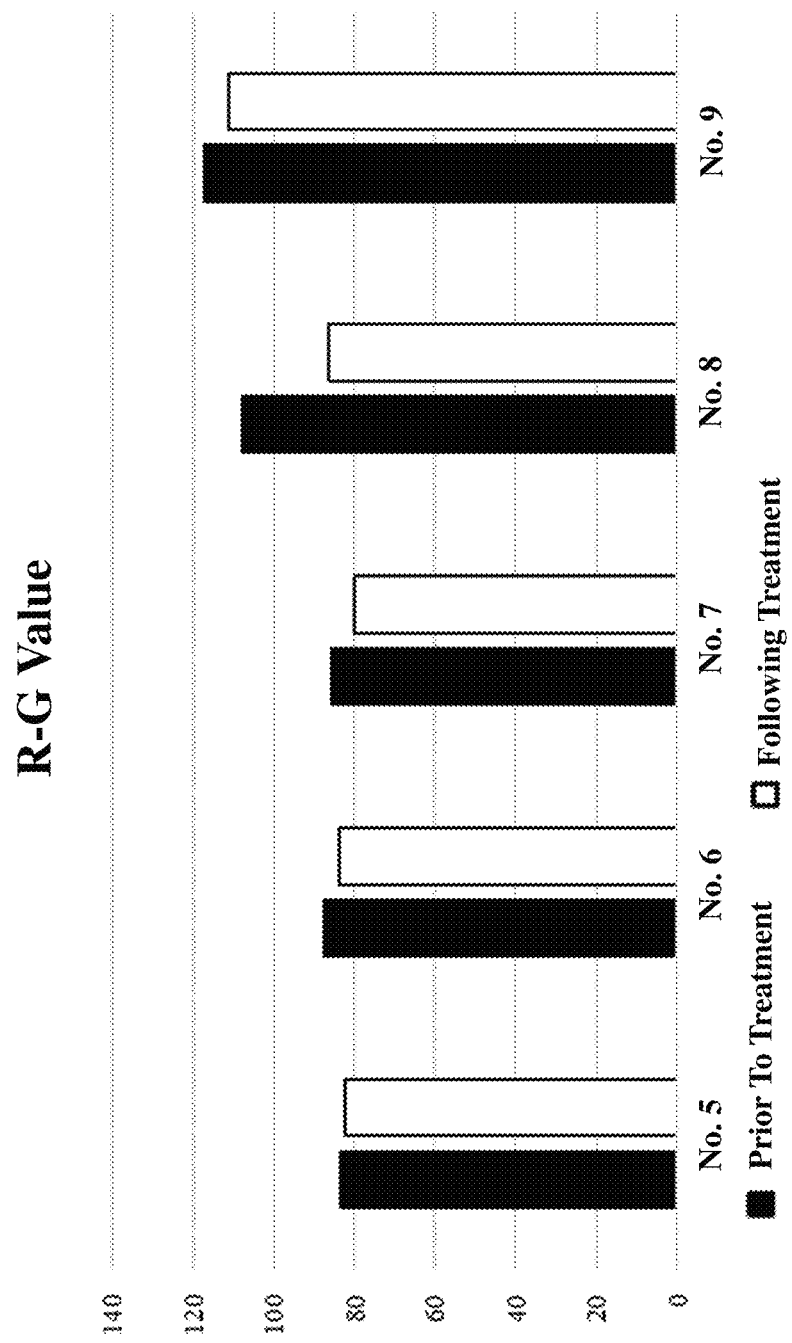
FIG. 10 is a statistical chart illustrating the R-G values of individuals Nos. 5-9 prior to treatment and following treatment.

Dr. Po-Han Huang provided polarized skin pictures and non-polarized skin pictures from 5 individuals, and then numbered them as Nos. 5-9 respectively. All individuals were diagnosed according these non-polarized pictures, wherein individuals No. 5-7 were suffered from telangiectasia, and individuals No. 8-9 were suffered from hemangioma. After all individuals received treatment, their polarized skin pictures and non-polarized skin pictures were captured. All individuals' treatment condition was diagnosed according these non-polarized skin pictures, and according to the procedure described in EXAMPLE 1, the R-G value prior to treatment and that following treatment of all individuals were obtained. The disease condition of Nos. 5-7 individuals was soothed; as shown in FIG. 10, the R-G value of each of them following treatment is lower than that prior to treatment. The disease condition of Nos. 8-9 individuals was soothed; as shown in FIG. 10, the R-G value of each of them following treatment is lower than that prior to treatment.

As above, the bracket of the R-G value accords with the diagnosis result made with the physicians' expertise, and therefore can be used as a reference for determining the disease severity based on intensity of redness of the skin.

Example 4

Dr. Po-Han Huang provided polarized skin pictures and non-polarized skin pictures from an individual of skin type 3. After the individual received the treatment, polarized skin pictures and non-polarized skin pictures were captured.

Figure 11:
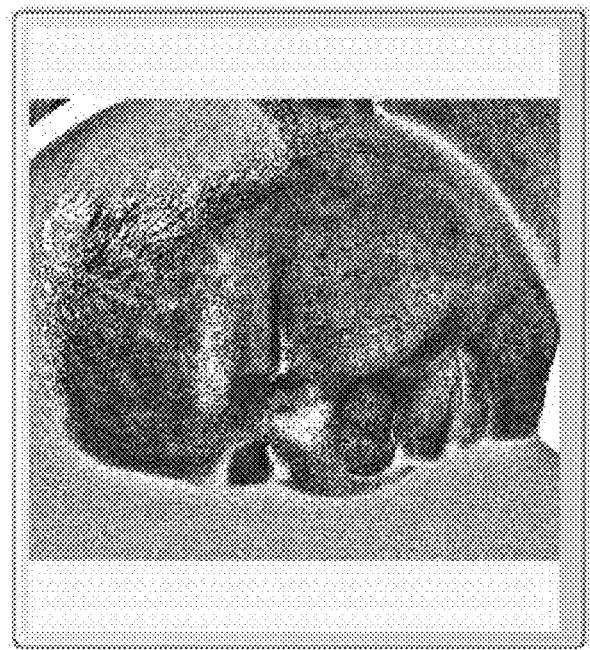
FIG. 11 is a schematic drawing illustrating a Brown component image obtained through RBX color-space transformation and its corresponding grayscale image.
Figure 11:
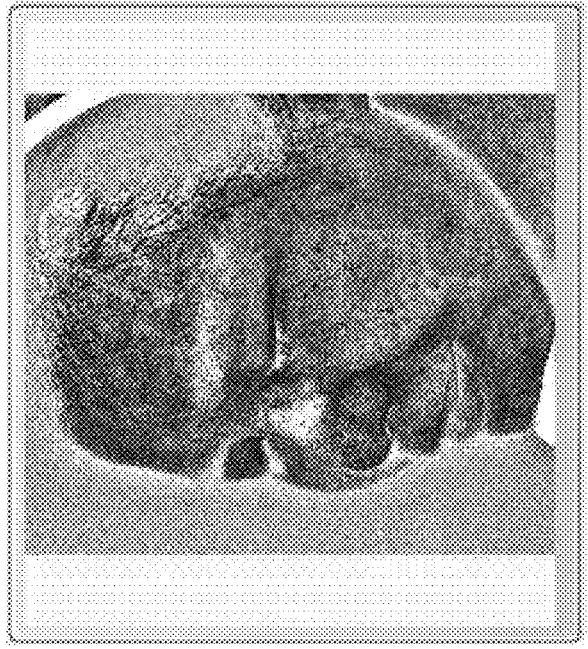

All polarized pictures were converted into Brown component pictures with RBX color-space transformation. After the Brown component pictures were, shown in FIG. 11, converted into gray scale pictures with LabVIEW, the grayscale pictures are transformed into grayscale intensity spectra. After the intensity values of 0-255 were divided equally into five value ranges, the five blocks corresponding to the five value ranges in each grayscale intensity spectrum were named as L0-L4 from small to large, i.e. L4 corresponding to the brightest intensity, and L0 corresponding to the darkest intensity. After the area of each block was calculated to be the total intensity of the corresponding block, the ratio of each block relative to the total area of all blocks in the same spectrum was calculated.

Figure 12:
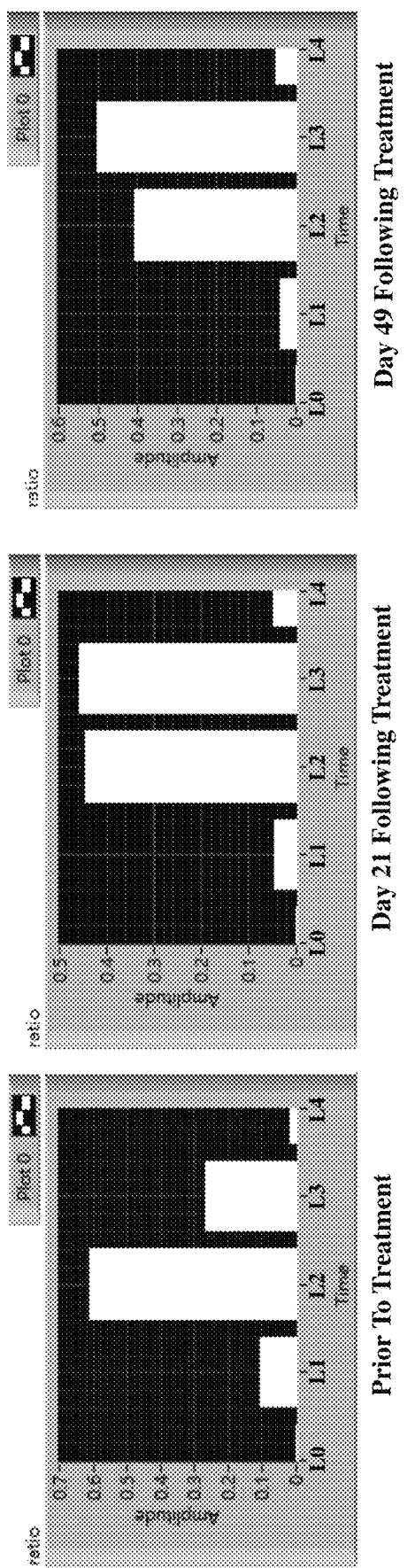
FIG. 12 is a statistical chart illustrating the area ratio of each block (L0-L4) relative to the total area of all blocks in the intensity spectrum of the individual of skin type 3 at different stages.

As shown in FIG. 12, the L1 ratio prior to treatment is greater than that following treatment, the L2 ratio prior to treatment is greater than that following treatment, and the L3 ratio prior to treatment is lower than that following treatment. This indicates the grayscale pictures following treatment tended to brighten. Additionally, the doctor determined that the treatment had whitening effect or fleck removal effect on the individual with visual observation.

As above, the intensity ratio of a block in a gray scale intensity spectrum can be used as a reference for determining effect on whitening or fleck removal.

Example 5

Dr. Po-Han Huang provided polarized skin pictures and non-polarized skin pictures from 3 individuals, one having nevus of Ota, another suffered from seborrheic keratosis, and the other having melasma. After all individuals received the treatment, their polarized skin pictures and non-polarized skin pictures were captured. All polarized pictures were converted into Brown component pictures with RBX color-space transformation. After the Brown component pictures were converted into grayscale pictures with LabVIEW, the grayscale pictures were transformed into grayscale intensity spectra. After the intensity values of 0-255 were divided equally into five value ranges, the five blocks corresponding to the five value ranges in each grayscale intensity spectrum were numbered as L0-L4 from small to large, i.e. L4 corresponding to the brightest intensity, and L0 corresponding to the darkest intensity. After the area of each block was calculated to be the total intensity of the corresponding block, the ratio of each block relative to the total area of all blocks in the same spectrum was calculated.

Figure 13:
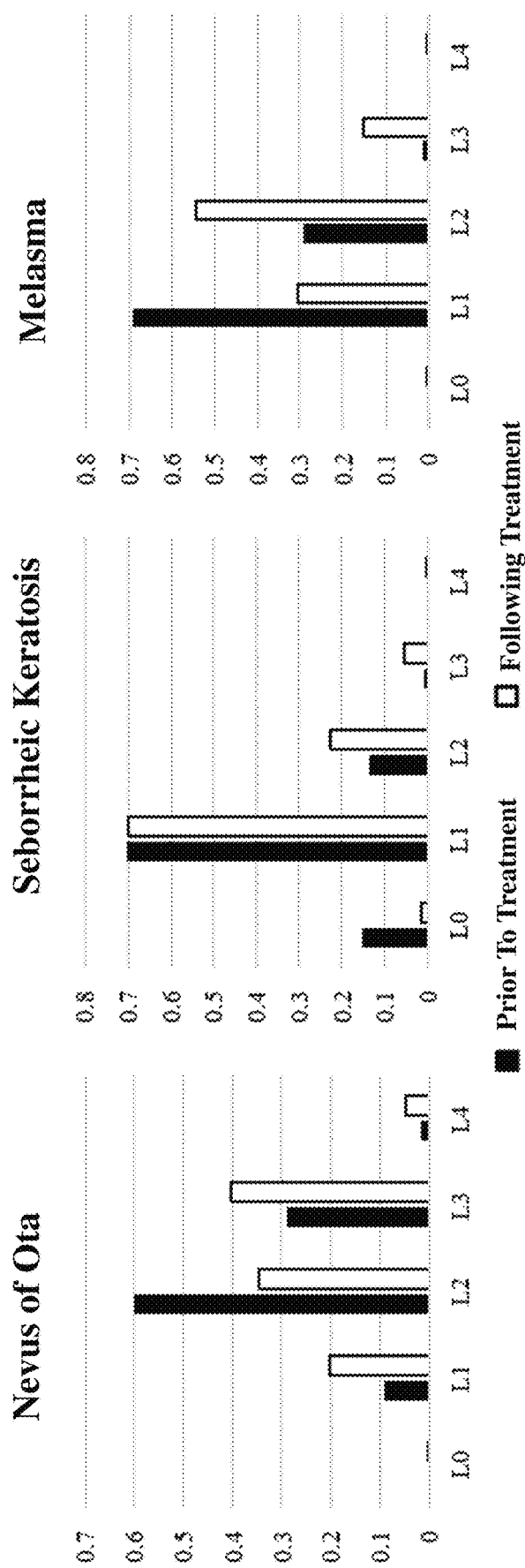
FIG. 13 is a statistical chart illustrating the area ratio of each block (L0-L4) relative to the total area of all blocks in the intensity spectrum of different individuals at different stages.

As shown in FIG. 13, in the individual having nevus of Ota, the L2 ratio prior to treatment is greater than that following treatment, and the L4 ratio prior to treatment is lower than that following treatment. This indicates the grayscale pictures following treatment tended to brighten. Additionally, the doctor determined that the treatment had nevus of Ota removal effect on the individual with visual observation.

As shown in FIG. 13, in the individual suffered from seborrheic keratosis, the L0 ratio prior to treatment is greater than that following treatment, the L1 ratio prior to treatment is almost equivalent to that following treatment, the L2 ratio prior to treatment is lower than that following treatment, and the L3 ratio prior to treatment is lower than that following treatment. This indicates the grayscale pictures following treatment tended to brighten. Additionally, the doctor determined that the treatment had seborrheic keratosis improvement effect on the individual with visual observation.

As shown in FIG. 13, in the individual having melasma, the L1 ratio prior to treatment is greater than that following treatment, the L2 ratio prior to treatment is lower than that following treatment, and the L3 ratio prior to treatment is lower than that following treatment. This indicates the grayscale pictures following treatment tended to brighten. Additionally, the doctor determined that the treatment had melasma removal effect on the individual with visual observation.

As above, the intensity ratio of a block in a grayscale intensity spectrum can be used as a reference for determining effect on skin disease improvement, either whitening or complete spots removal.

While the invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A method for estimating skin therapy effect, comprising:

decomposing a skin image obtained prior to skin therapy and another skin image obtained following skin therapy through RBX color-space transformation respectively into a Brown component image prior to skin therapy and another Brown component image following skin therapy;

performing gray processing on the Brown component image prior to skin therapy and the Brown component image following skin therapy respectively to generate a grayscale image prior to skin therapy and another grayscale image following skin therapy;

transforming the grayscale image prior to skin therapy and the grayscale image following skin therapy respectively into an intensity spectrum prior to skin therapy and another intensity spectrum following skin therapy;

partitioning each intensity spectrum into a first block and a second block according to an intensity values, wherein the intensity value corresponding to the first block is greater than that corresponding to the second block;

calculating an area of the first block in the intensity spectrum prior to skin therapy, an area of the second block in the intensity spectrum prior to skin therapy, an area of the first block in the intensity spectrum following skin therapy, and an area of the second block in the intensity spectrum following skin therapy; and dividing the area of the first block in the intensity spectrum prior to skin therapy by an area of total blocks in the intensity spectrum prior to skin therapy to generate a Pre-H ratio value, dividing the area of the second block in the intensity spectrum prior to skin therapy by the area of total blocks in the intensity spectrum prior to skin therapy to generate a Pre-L ratio value, dividing the area of the first block in the intensity spectrum following skin therapy by an area of total blocks in the intensity spectrum following skin therapy to generate a Post-H value, and dividing the area of the second block in the intensity spectrum following skin therapy by the area of total blocks in the intensity spectrum following skin therapy to generate a Post-L value, wherein while the Post-H value is greater than the Pre-H value and the Post-L value is less than the Pre-L value, it indicates that the skin therapy is effective.

2. The method as claimed in claim 1, wherein the skin therapy is provided for improving degree of skin redness, enhancing skin whitening degree, or lowering skin fleck degree.

3. The method as claimed in claim 2, wherein the skin redness is related to a skin disease with vascular involvement, including inflammatory dermatoses and a skin disease with vascular dilation but no inflammation, and each skin disease is rosacea, psoriasis, atopic dermatitis, facial eczema, sensitive skin of face, seborrheic dermatitis, dermatophytosis, pityriasis versicolor, hemangioma, aging skin with vessel dilation, skin cancer, acne, seborrheic keratosis, or telangiectasia.

4. The method as claimed in claim 2, wherein the skin fleck is nevus of Ota or, melasma, or pigmented aging spots, including solar lentigines.

5. The method as claimed in claim 1, wherein the captured skin image is a color image.

6. The method as claimed in claim 1, wherein the skin therapy is 755 nm picosecond toning laser therapy, 1064 nm picosecond toning laser therapy, or 755 nm picosecond spot laser therapy.

* * * * *